United States Patent [19]

Kishimoto et al.

[11] Patent Number: 4,994,478
[45] Date of Patent: Feb. 19, 1991

[54] OXADIAZOLE DERIVATIVE

[75] Inventors: Takashi Kishimoto; Takashi Okabe; Tomio Yamada; Michihiko Matsuda; Yukio Kitagawa, all of Odawara, Japan

[73] Assignee: Nippon Soda Co., Ltd., Tokyo, Japan

[21] Appl. No.: 357,623

[22] Filed: May 18, 1989

Related U.S. Application Data

[63] Continuation of Ser. No. 136,190, Dec. 21, 1987, abandoned.

[30] Foreign Application Priority Data

Dec. 27, 1986 [JP] Japan .................. 61-310145

[51] Int. Cl.$^5$ .............. C07D 271/06; A01N 43/82
[52] U.S. Cl. ............................... 514/364; 548/131
[58] Field of Search ................ 548/131; 514/364

[56] References Cited

U.S. PATENT DOCUMENTS 4,632,983  12/1980  Lamm ..................... 534/772

FOREIGN PATENT DOCUMENTS 713052  7/1965  Canada .

Primary Examiner—Robert Gerstl
Attorney, Agent, or Firm—George B. Oujevolk

[57] ABSTRACT

The present invention relates to a compound having the formula

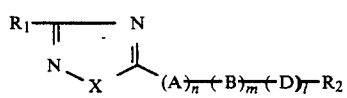

(wherein $R_1$ denotes a phenyl radical (which may be substituted by halogen atoms, $C_{1-6}$ alkyl radicals, $C_{1-6}$ alkoxy radicals (which may be substituted by $C_{1-6}$ alkoxy radicals,) $C_{2-6}$ alkynyloxy radicals, amino radicals, nitro radicals, phenyl radicals, phenoxy radicals or $C_{1-6}$ alkylthio radicals), a five or six membered heterocyclic radical (which may be substituted by halogen atoms or $C_{1-6}$ alkyl radicals), a $C_{1-6}$ alkyl radical (which may be substituted by aryl radicals) or

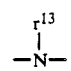

wherein each or $r^1$ and $r^2$ denotes a $C_{1-6}$ alkyl radical or a phenyl radical)

X denotes oxygen atom or sulfur atom;

A denotes

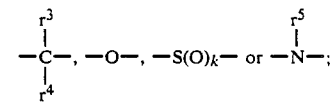

B denotes

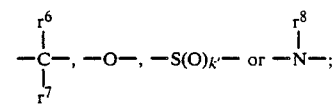

D denotes

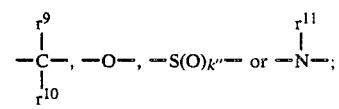

n, m and l denote 0 or 1, (wherein $r^3$, $r^4$, $r^6$, $r^7$, $r^9$ and $r^{10}$, respectively, denotes hydrogen atom, halogen atom, $C_{1-6}$ alkyl radical, the radical expressed by the formula —Y— $r^{12}$ (wherein $r^{12}$ denotes hydrogen atom, cyano radical, $C_{1-6}$ alkyl radical (which may be substituted by $C_{1-6}$ alkoxycarbonyl radicals,) cycloalkyl radical, $C_{1-6}$ alkoxycarbonyl radical, $C_{1-6}$ alkylcarbamoyl radical, $C_{1-6}$ alkylthiocarbamoyl radical, phenylcarbamoyl radical (which may be substituted by halogen atom), phenylthiocarbamoyl radical (which may be substituted by halogen atoms), or $C_{1-6}$ alkylcarbonyl radical (which may be substituted by halogen atoms); Y denotes oxygen atom, sulfur atom, —SO—, —SO$_2$—, or the radical expressed by the formula

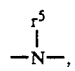

($r^{13}$: hydrogen atom, $C_{1-6}$ alkyl radical)), or oxo-radicals or the radical expressed by the formula $NOr^{14}$ where $r^3$ or $r^4$; $r^6$ and $r^7$ or $r^9$ and $r^{10}$ are combined (wherein $r^{14}$ denotes hydrogen atom, $C_{1-6}$ alkyl radical, $C_{1-6}$ alkylcarbonyl radical, or $C_{1-6}$ alkylcarbamoyl radical), provided, however, that $r^6$ may form a double bond in combination with $r^3$ or $r^9$; k, k' and k" denote 0, 1 or 2, respectively;

$r^5$, $r^8$ and $r^{11}$ each denote hydrogen atom or $C_{1-6}$ alkyl radical;

When A is $$-\underset{|}{N}-\underset{r^5}{}$$

however, m denotes 1. Further, A and B, or B and D do not simultaneously denote oxygen atoms or sulfur atoms.)

$R_2$ denotes a phenyl radical (which may be substi- (Abstract continued on next page.)

tuted by —Z—r$^{15}$ (wherein r$^{15}$ denotes hydrogen atom, C$_{1-6}$ alkyl radical (which may be substituted by C$_{1-6}$ alkoxycarbonyl radicals or halogen atoms), phenyl radicals, cycloalkyl radicals, the pyridyl radicals (which may be substituted by halogen atoms or C$_{1-6}$ haloalkyl radicals), C$_{1-6}$ alkylcarbamoyl radicals, or C$_{1-6}$ alkylcarbonyl radicals; Z denotes oxygen atom, sulfur atom or the radicals expressed by the formula

(wherein r$^{14}$ denotes hydrogen atom or C$_{1-6}$ alkyl radical), C$_{1-6}$ alkyl radicals, halogen atoms or nitro radicals), a cycloalkyl radical, a naphthyl radical, a benzthiazolyl radical (which may be substituted by C$_{1-6}$ alkoxy radicals or C$_{1-6}$ alkylamino radicals or halophenylamino radicals), or a C$_{1-6}$ alkyl radical which may be substituted by halogen atoms);

its producing processes and an acaricidal composition comprising its compound as active ingredient(s).

12 Claims, No Drawings

OXADIAZOLE DERIVATIVE

DESCRIPTION

1. Technical Field

The present invention relates to new oxa(thia)diazole derivatives having an excellent acaricidal activity, their manufacturing processes and the acaricides made therefrom.

2. Background Art

To control acaricides, organophosphorous compounds, dinitrotype compounds or a variety of other compounds have been used. In recent years, however, there have emerged mites resistant to these chemicals, and as a result the advent of a new type of acaricides has been desired.

The following compound is known as a compound having an acaricidal activity and the oxadiazole skeleton similar to the compounds of this invention.

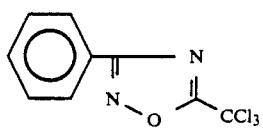

(Canadian patent No. 713052)

The purpose of this invention is to offer agricultural chemicals which can be advantageously synthesized on a commercial basis and which are capable of safe use with positive effects.

DISCLOSURE OF INVENTION

The present invention relates to the compounds having the following formula, their manufacturing methods and the acaricides containing said compound(s) as active ingredients:

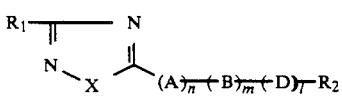

(wherein $R_1$ denotes a phenyl radical (which may be substituted by halogen atoms, $C_{1-6}$ alkyl radicals, $C_{1-6}$ alkoxy radicals (which may be substituted by $C_{1-6}$ alkoxy radicals,) $C_{2-6}$ alkynyloxy radicals, amino radicals, nitro radicals, phenyl radicals, phenoxy radicals or $C_{1-6}$ alkylthio radicals), a five or six menbered heterocyclic radical (which may be substituted by halogen atoms $C_{1-6}$ alkyl radicals), a $C_{1-6}$ alkyl radical (which may be substituted by aryl radicals) or

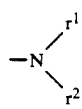

(wherein each of $r^1$ and $r^2$ denotes a $C_{1-6}$ alkyl radical or a phenyl radical)

X denotes oxygen atom or sulfur atom;

A denotes

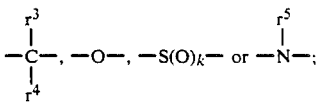

B denotes

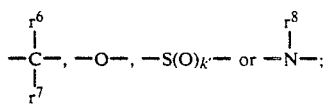

D denotes

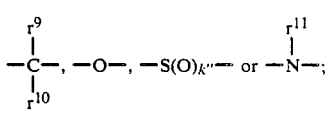

n, m and l each denote 0 or 1, (wherein $r^3$, $r^4$, $r^6$, $r^7$, $r^9$ and $r^{10}$, respectively, denotes hydrogen atom, halogen atom, $C_{1-6}$ alkyl radical, the radical expressed by the formula $-Y-r^{12}$ (wherein $r^{12}$ denotes hydrogen atom, cyano radical, $C_{1-6}$ alkyl radical (which may be substituted by $C_{1-6}$ alkoxycarbonyl radicals,) cycloalkyl radical, $C_{1-6}$ alkoxycarbonyl radical, $C_{1-6}$ alkylcarbamoyl radical, $C_{1-6}$ alkylthiocarbamoyl radical, phenylcarbamoyl radical (which may be substituted by halogen atom), phenylthiocarbamoyl radical (which may be substituted by halogen atoms), or $C_{1-6}$ alkylcarbonyl radical (which may be substituted by halogen atoms); Y denotes oxygen atom, sulfur atom, $-SO-$, $-SO_2-$, or the radical expressed by the formula

($r^{13}$ hydrogen atom, $C_{1-6}$ alkyl radical)), or oxo-radicals or the radical expressed by the formula $NOr^{14}$ where $r^3$ and $4^4$; $r^6$ and $r^7$ or $r^9$ and $r^{10}$ are combined (wherein $r^{14}$ denotes hydrogen atom, $C_{1-6}$ alkyl radical, $C_{1-6}$ alkylcarbonyl radical, or $C_{1-6}$ alkylcarbamoyl radical), provided, however, that $r^6$ may form a double bond in combination with $r^3$ or $r^9$; k, k' and k" denote 0, 1 or 2, respectively;

$r^5$, $r^8$ and $r^{11}$ each denote hydrogen atom or $C_{1-6}$ alkyl radical;

When A is

however, m denotes 1. Further, A and B, or B and D do not simultaneously denote oxygen atoms or sulfur atoms.)

$R_2$ denotes a phenyl radical (which may be substituted by $-Z-r^{15}$ (wherein $r^{15}$ denotes hydrogen atom, $C_{1-6}$ alkyl radical (which may be substituted by $C_{1-6}$ alkoxycarbonyl radicals or halogen atoms), phenyl radicals, cycloalkyl radicals, the pyridyl radicals (which may be substituted by halogen atoms or $C_{1-6}$ haloalkyl radicals), $C_{1-6}$ alkylcarbamoyl radicals, or $C_{1-6}$ alkylcarbonyl radicals; Z denotes oxygen atom, sulfur atom or the radicals expressed by the formula

(wherein $r^{16}$ denotes hydrogen atom or $C_{1-6}$ alkyl radical), $C_{1-6}$ alkyl radicals, halogen atoms or nitro radicals), a cycloalkyl radical, a naphthyl radical, a benzthiazolyl radical (which may be substituted by $C_{1-6}$ alkoxy radicals or a $C_{1-6}$ alkylamino radicals or halophenylamino radicals), or $C_{1-6}$ alkyl radical which may be substituted by halogen atoms).

The compounds of the invention are effective against desert spider mite, two-spotted spider mite, citrus red mite and a variety of other phytophagous mites on plants. At the ovular, larval and nymphal stages of a variety of mites, in particular, these compounds exhibit excellent ovicidal, larvicidal and nymphocidal activities. Their toxicity to warmblooded animals is low and their safety high.

BEST MODE FOR CARRYING OUT THE INVENTION The compounds of the invention can be manufactured in compliance with the following reaction schemes.

(1) Manufacturing method

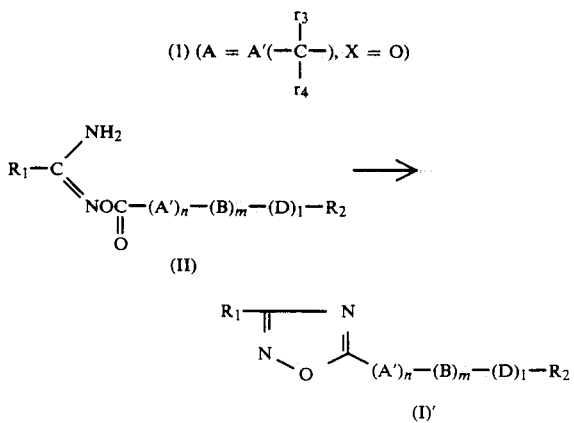

Reactions are allowed to proceed for 30 minutes to 5 hours at 50° C.-200° C. in an organic solvent. For the solvent, DMF, xylene, dichlorobenzene, etc. can be used.

(2) Manufacturing method

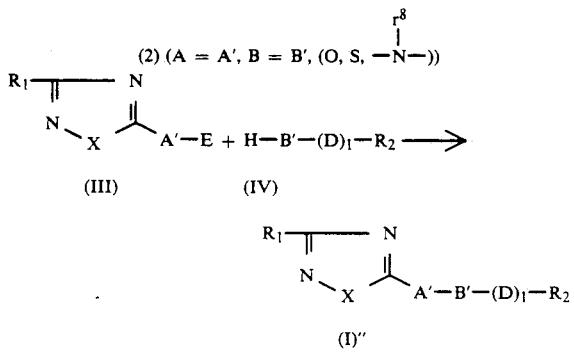

(where E denotes halogen atoms or $C_{1-6}$ alkoxy radicals) Reactions are allowed to go in an organic solvent for 1 hour to several tens of hours at a temperature of 0° C. to boiling point of the solvent used, in the presence, if desired, of a base. For the solvent, benzene, toluene, etc. may be used. For the base, pyridine, toluene, etc. may be used.

(3) Manufacturing method

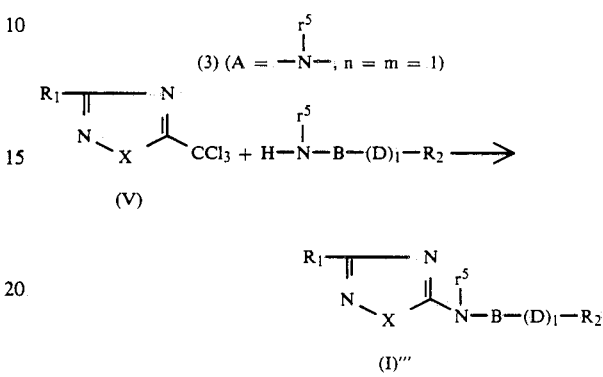

Reactions are allowed to go in methanol or any other suitable organic solvent for 1 hour to 10 hours at a temperature of 50° C. to the boiling point of the solvent used.

(4) Manufacturing method

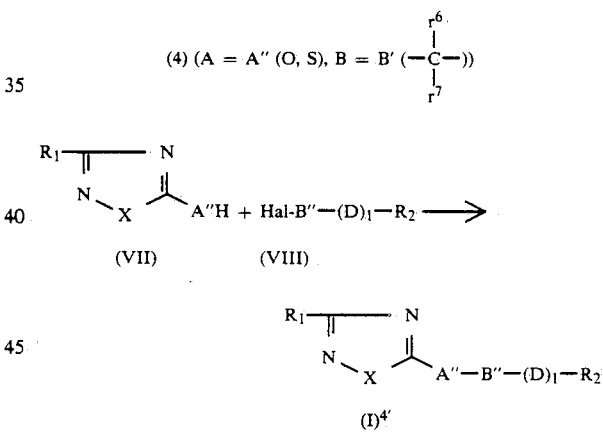

Reactions are allowed to go in DMF or any other suitable organic solvent for 30 minutes to 5 hours at a temperature of −20° C. to 50° C. and in the presence of a base. For the base, triethylamine, pyridine, etc. may be used. It is also possible to use sodium hydride etc. to produce beforehand a sodium salt of the compound having the formula (VII) and after this to allow this sodium salt to react with the compound having the formula (VIII).

(5) Manufacturing method (5) (A=A')

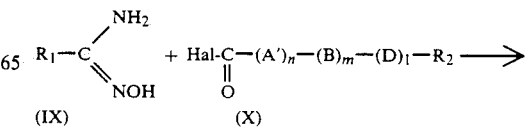

-continued

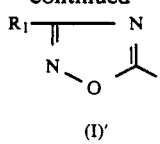

(I)′

Condensation reactions are allowed to go in acetonitrile or any other suitable organic solvent, at a temperature of 0° C. to the boiling point of the solvent used and in the presence of a base. When this ends, if desired, the reaction solution is allowed to undergo cyclization reaction under heat. In the cyclization reaction are used acetonitrile, DMF, xylene, dichlorobenzene or other solvent.

(6) Manufacturing method (6) (A=A″, B=B″)

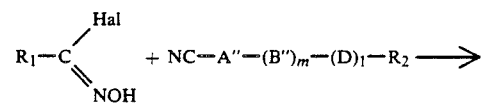

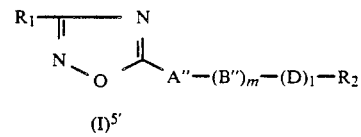

Reactions are allowed to go in diethyl ether or any one of other suitable organic solvents, in the presence of a base, such as triethyleneamine for a period of 1 hour to several tens of hours, at a temperature of $-20°$ C. to $50°$ C.

(7) Further, depending on the type of substituents of $R_1$, A, B, D and $R_2$, the compounds of this invention can also be manufactured by following the reaction scheme below or by suitably choosing known and similar reactions.

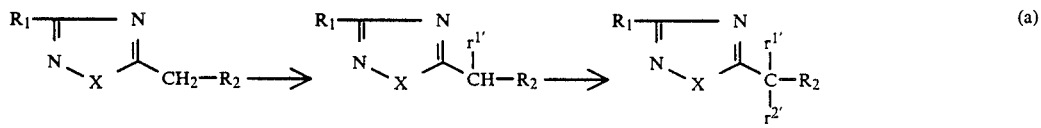

(where $r^{1'}$ and $r^{2'}$ each denote $C_{1-6}$ alkyl radicals)

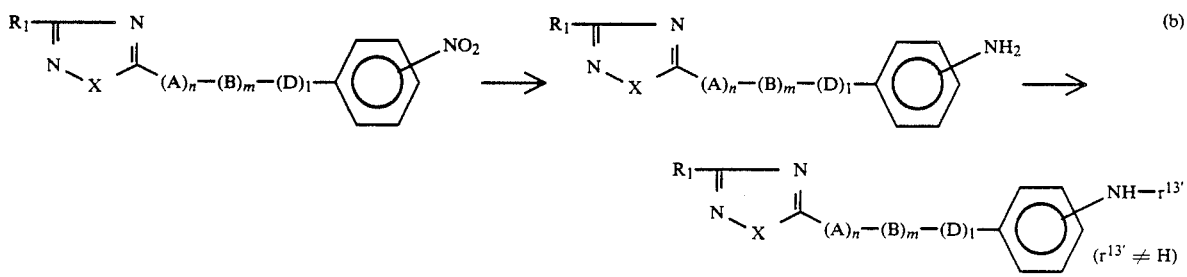

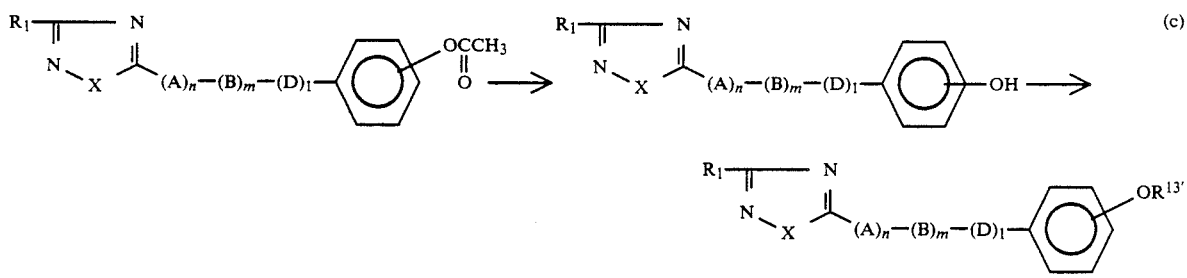

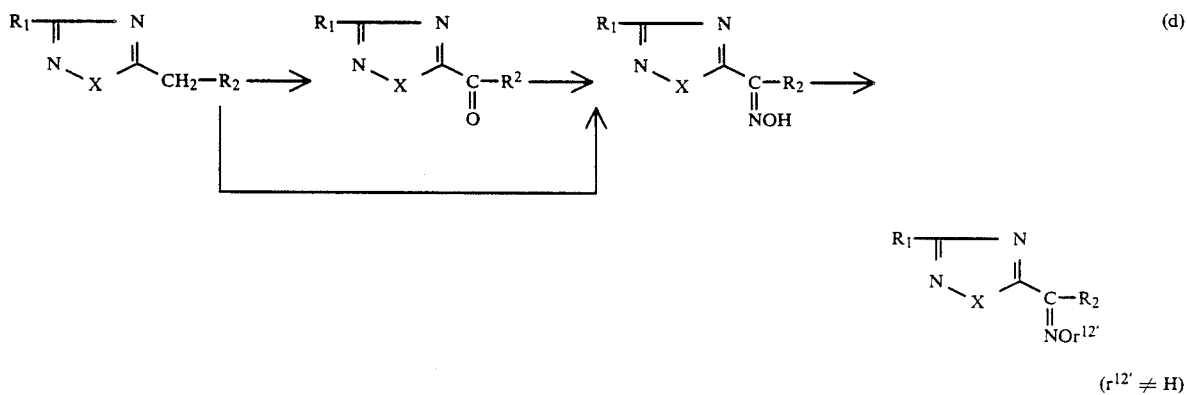

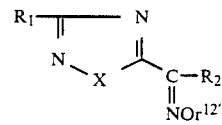

($r^{12'} \neq H$)

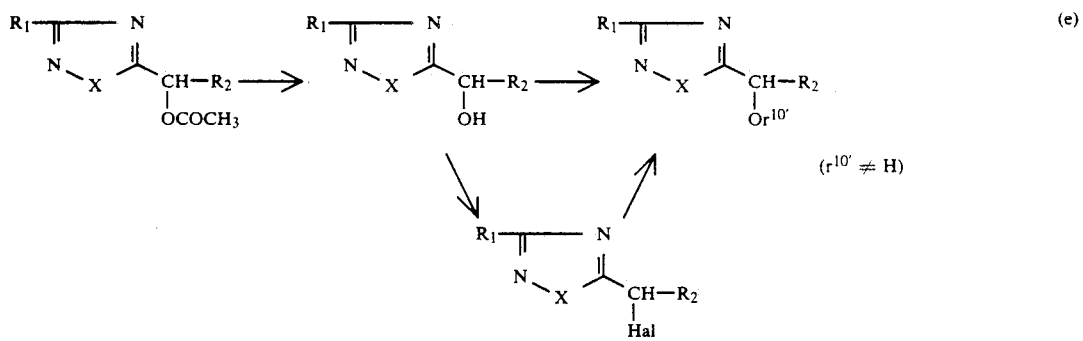

In whichever methods these reactions are allowed to proceed, normal after-treatments on completion of the reactions produce specified substance in good yields. The structure of the compounds of this invention has been determined by IR, NMR, MASS, etc. Depending on the type of substituents, some of the compounds of this invention have isomers, which this invention shall invariably cover.

The following examples illustrate the present invention.

EXAMPLE 1

3-(2,6-dichlorophenyl)-5-(4-isopropoxybenzyl)-1,2,4-oxadiazole (Compound No. 10)

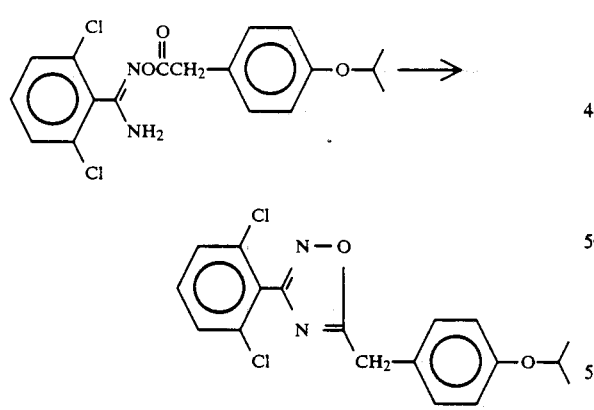

A solution of 102.5 g of N'-(4-isopropoxyphenylacetoxy)-2,6-dichlorobenzamidine in 500 ml of DMF was heated at 140° C. for 1.5 hours.

After cooling, the solution was poured into 2 kg of ice, and extracted several times with ethyl acetate. The collected extracts were washed with water, dried over anhydrous magnesium colorised with chacoal and evaporated under reduced pressure.

The residue was washed with ligroin, then with cold absolute methanol to give 64.7 g of Compound No. 10. m.p. 67°–68° C.

EXAMPLE 2

3-(2,6-dichlorophenyl)-5-(4-t-butylanilinomethyl)-1,2,4-oxadiazole (Compound No. 68)

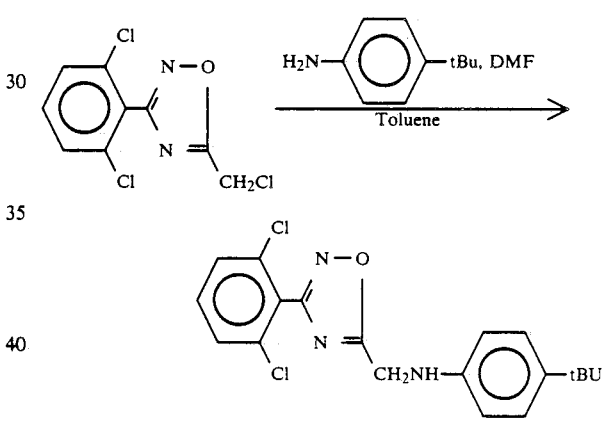

To a solution of 1 g of 3-(2,6-dichlorophenyl)-5-chloromethyl-1,2,4-oxadiazole in 10 ml of toluene, 1,13 g of 4-t-butylaniline and 2 ml of DMF were added, and the mixture was heated under reflux over night.

After cooling, the reaction mixture was poured into water, extracted with ethyl acetate and the extract was dried over anhydrous magnesium sulfate, evaporated under reduced pressure.

The residue obtained was purified by silica gel column chromatography to give 1.1 g of Compound No. 68. m.p. 104–106° C.

EXAMPLE 3

3-(2,6-dichlorophenyl)-5-cyclohexylcarbamoyl-1,2,4-oxadiazole (Compound No. 114)

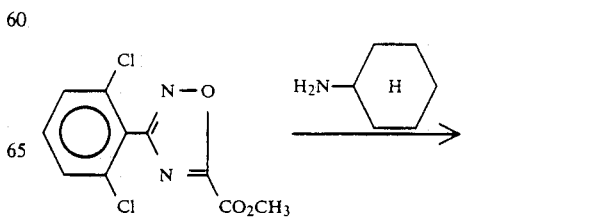

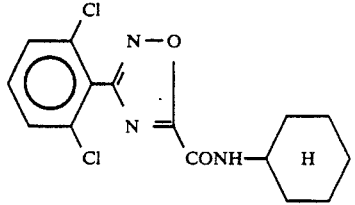

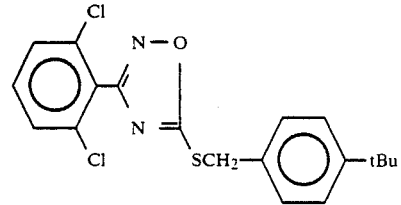

To a solution of 1 g of 3-(2,6-dichlorophenyl)-5-methoxycarbonyl-1,2,4-oxadiazole in 5 ml of toluene, was added 0.4 g of cyclohexylamine at room temperature.

After 3 hours, the reaction mixture was evaporated under reduced pressure, and the residue was purified by silica gel column chromatography to give 1.1 g of Compound No. 114. m.p. 153–155° C.

EXAMPLE 4

3-(2,6-dichlorophenyl)-5-(4-chlorobenzylamine)-1,2,4-oxadiazole (Compound No. 66)

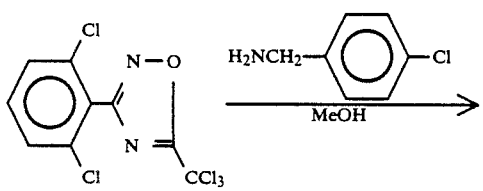

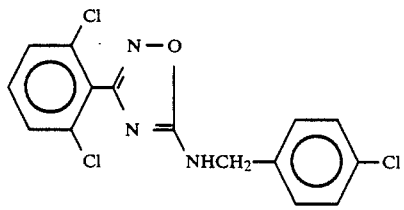

To a solution of 1 g of 3-(2,6-dichlorophenyl)-5-trichloromethyl-1,2,4-oxadiazole in 10 ml of absolute methanol was added 0.5 g of 4-chlorobenzylamine at room temperature, and the mixture was heated under reflux for 10 hours.

The reaction mixture was then evaporated under reduced pressure and the residue was purified by column chromatography on silica gel to give 0.55 g of Compound No. 66. m.p. 148–150° C.

EXAMPLE 5

3-(2,6-dichlorophenyl)-5-(4-t-butylbenzylthio)-1,2,4-oxadiazole (Compound No. 64)

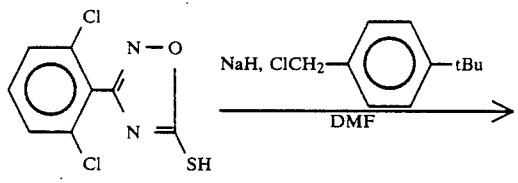

To a solution of 0.6 g of 3-(2,6-dichlorophenyl)-5-mercapto-1,2,4-oxadiazole in 10 ml of DMF was added 0.11 g of 60% sodium hydride under cooling.

After one hour of stirring at room temperature, 0.5 g of 4-t-butylbenzyl chloride was added to the reaction mixture under cooling.

After 3 hours of stirring at room temperature, the reaction mixture was poured into ice-water, extracted with ethyl acetate and the extracted was washed with water, dried over anhydrous magnesium sulfate and evaporated under reduced pressure.

The residue obtained was purified by silica gel column chromatography to give 0.5 g of Compound No. 64. $N_D^{25} 1.5893$.

EXAMPLE 6

3-phenyl-5-benzoyl-1,2,4-oxadiazole (Compound No. 76)

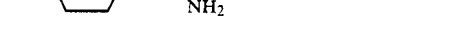

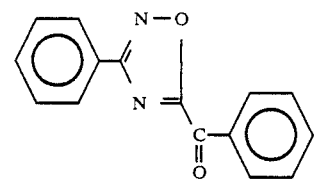

To a solution of 2.5 g of N-hydroxybenzamidine in 20 ml of acetonitrile, 3.41 g of phenylglyoxyl chloride was added under cooling, and then 1.6 g of pyridine was added.

After 2 hours of stirring at room temperature, acetonitrile was distilled off under reduced pressure. The residue was extracted with ethyl acetate and the extract was washed with water, dried over anhydrous magnesium sulfate and after filtration ethyl acetate was evaporated under reduced pressure.

The residue obtained was purified by silica gel column chromatography to give 2.3 g of Compound No. 76. $n_D^{24.5} 1 6119$.

EXAMPLE 7

3-(2,6-dichlorophenyl)-5-(α-methyl-4-isopropoxybenzyl)-1,2,4-oxadiazole (Compound No. 61)

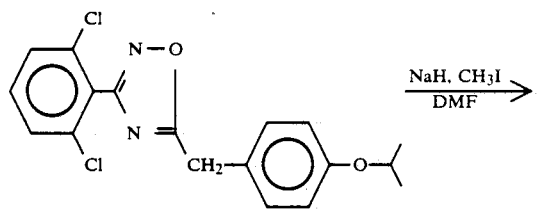

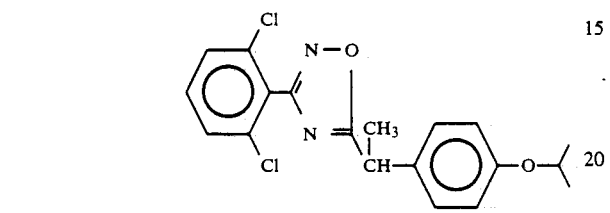

To a solution of 3 g of 3-(2,6-dichlorophenyl)-5-(4-isopropoxybenzyl)-1,2,4-oxadiazole in 20 ml of DMF was added 0.33 g of 60% sodium hydride below −5° C.

After 2 hours of stirring at the same temperature, 1.2 g of methyl iodide was added to the solution, followed by stirring for 4 hours at room temperature.

The reaction mixture was then poured into ice-water, extracted with ethyl acetate and the extract was washed with water, dried over anhydrous magnesium sulfate and after filtration ethyl acetate was evaporated under reduced pressure.

The residue was purified by silica gel column chromatography to give 2.3 g of Compound No. 61. m.p. 84–86° C.

EXAMPLE 8

3-(2,6-dichlorophenyl)-5-(4-(1-ethoxycarbonylethoxy)benzyl)-1,2,4-oxadiazole (Compound No. 33)

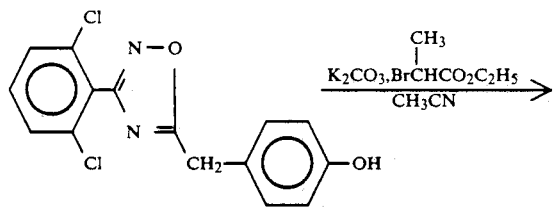

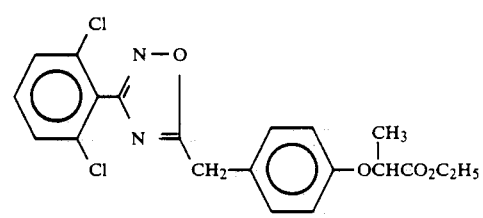

To a solution of 0.7 g of 3-(2,6 dichlorophenyl)-5-(4-hydroxybenzyl)-1,2,4-oxadiazole in 10 ml of acetonitrile, 0.31 g of anhydrous potassium carbonate and 0.45 g of ethyl 2-bromopropionate were added at room temperature.

The suspension solution was then heated under reflux over night.

After cooling, the reaction mixture was poured into water, extracted with ethyl acetate and the extract was washed with water, dried over anhydrous magnesium sulfate and after filtration ethyl acetate was evaporated under reduced pressure.

The residue obtained was purified by silica gel column chromatography to give 0.9 g of Compound No. 33. m.p. 90–92° C.

EXAMPLE 9

3-(2,6-dichlorophenyl)-5-(α-hydroxyimino)-4-isopropoxybenzyl)-1,2,4-oxadiazole (Compound Nos. 106, 107)

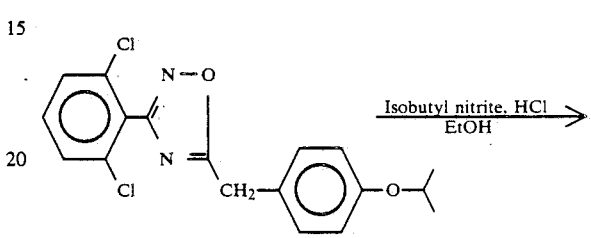

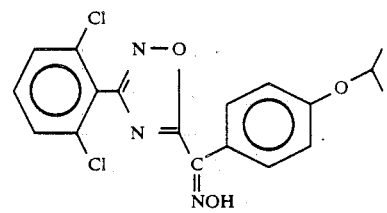

To a suspension of 8 g of 3-(2,6-dichlorophenyl)-5-4-isopropoxybenzyl)-1,2,4-oxadiazole in 80 ml of absolute ethanol was added dropwise a solution of 5.2 g of isobutylnitrite in 5 ml of absolute ethanol with bubbling gaseous hydrogen chloride at room temperature.

After the addition of isobutylnitrite was completed, gaseous hydrogen chloride passed into the suspension for an additional 6 hours at the same temperature. The reaction mixture was then evaporated under reduced pressure, extracted with ethyl acetate and the extract was washed with water, dried over anhydrous magnesium sulfate and after filtration ethyl acetate was evaporated under reduced pressure.

The residue obtained was purified by silica gel column chromatography to give 1.6 g of Compound No. 106. m.p. 191–194 and 0.4 g of Compound No. 107. m.p. 146–149° C.

EXAMPLE 10

3-(2,6-dichlorophenyl)-5-(-(N methylcarbamoyloximino)-4-isopropoxybenzyl)-1,2,4-oxadiazole (Compound No. 110)

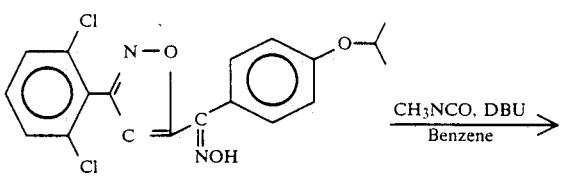

-continued

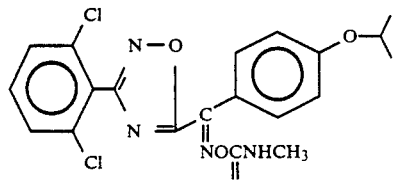

To a solution of 0.7 g of 3-(2,6-dichlorophenyl)-5-(4-isopropoxy-α-hydroxyiminobenzyl)-1,2,4-oxadiazole in 10 ml of benzene, 0.12 g of methyl isocyanate and one drop of DBU were added at room temperature.

After 3 hours, the reaction mixture was evaporated under reduced pressure and the residue was purified by silica gel column chromatography to give 0.5 g of Compound No. 110. m.p 123–125° C.

EXAMPLE 11

3-(2,6-dichlorophenyl)-5-(α-chloro-4-isopropoxybenzyl)-1,2,4-oxadiazole (Compound No. 101)

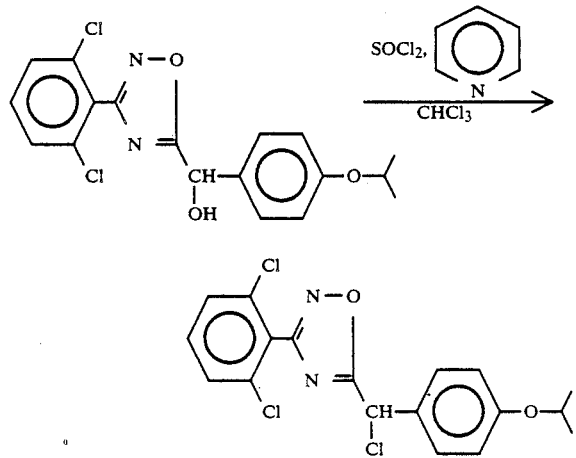

To a solution of 4 g of 3-(2,6-dichlorophenyl)-3-(4-isopropoxy-α-hydroxybenzyl)1,2,4oxadiazole in 12 ml of chloroform, 2.51 g of thionyl chloride and one drop of pyridine were added at room temperature.

After 1 hour of stirring the reaction mixture was heated under reflux for 30 minute and then evaporated under reduced pressure.

The residue was purified by column chromatography on silica gel to give 3.62 g of Compound No. 101. m.p 124–126° C.

EXAMPLE 12

3-(2,6-dichlorophenyl)-5-(4-t-butylbenzylthio)-1,2,4-thiadiazole (Compound No. 127)

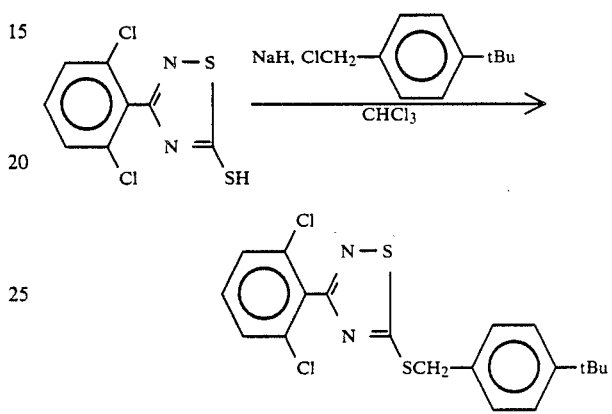

To a solution of 0.5 g of 3-(2,6-dichlorophenyl)-5-5-mercapto-1,2,4-thiadiazole in 5 ml of DMF was added 0.08 g of 60% sodium hydride at 0° C.

After 30 minutes of stirring at room temperature, 0.35 g of 4-t-butylbenzyl chloride was added dropwise to the suspension at 0° C.

After 2 hours of stirring at room temperature, the reaction mixture was poured into ice-water, extracted with ethyl acetate and the extract was washed with water, dried over anhydrous magnesium sulfate and evaporated under reduced pressure.

The residue obtained was purified by silica gel column chromatography to give 0.6 g of Compound No. 127. $n_D^{26}$ 1 6132.

Inclusive the above, each compound with the scope of the present invention which can be prepared in analogous method is tabulated in Table 1.

TABLE 1

Structural Formula $$R_1 \underset{N-X}{\overset{N}{\rightleftharpoons}} \genfrac{}{}{0pt}{}{-(A)n-(B)m-(D)l-R_2}{-(A)n-(B)m-(D)l-}$$

| Compound No. | R$_1$ | X | –(A)n–(B)m–(D)l– | R$_2$ | Physical Properties (°) m.p. |
|---|---|---|---|---|---|
| 1 | phenyl | O | –CH$_2$– | 4-OCH(CH$_3$)$_2$-phenyl | (30–31) |
| 2 | 4-Cl-phenyl | " | " | " | (67–68) |
| 3 | 3-Cl-phenyl | " | " | " | $n_D^{26}$ 1.3935 |
| 4 | 2-Cl-phenyl | " | " | " | $n_D^{26}$ 1.5717 |
| 5 | 4-CH$_3$-phenyl | " | " | " | (48–50) |
| 6 | 4-CH$_3$O-phenyl | " | " | " | (49–50) |
| 7 | 4-NO$_2$-phenyl | " | " | " | (83–85) |

TABLE 1-continued

Structural Formula $$R_1 \underset{N\diagdown X}{\overset{N}{\underset{\parallel}{=}}} \underset{-(A)n-(B)m-(D)l-}{\overset{(A)n-(B)m-(D)l-R_2}{\diagup}}$$

| Compound No. | R₁ | X | —(A)n—(B)m—(D)l— | R₂ | Physical Properties ( ) m.p. |
|---|---|---|---|---|---|
| 8 | biphenyl | " | " | " | (114–116) |
| 9 | 2,6-difluorophenyl | " | " | " | $n_D^{22}$ 1.3320 |
| 10 | 2,6-dichlorophenyl | " | " | " | (67–68) |
| 11 | 2,6-dibromophenyl | O | —CH₂— | 4-isopropoxyphenyl | $n_D^{26}$ 1.5915 |
| 12 | 2,6-dimethoxyphenyl | " | " | " | (128–130) |

TABLE 1-continued

Structural Formula $$R_1 \underset{N-X}{\overset{N}{\parallel}} \underset{-(A)n-(B)m-(D)l-}{\overset{(A)n-(B)m-(D)l-R_2}{\diagup}}$$

| Compound No. | $R_1$ | X | $R_2$ | Physical Properties ( ) m.p. |
|---|---|---|---|---|
| 13 | 2,6-dimethylphenyl | " | " | $n_D^{26}$ 1.5511 |
| 14 | 2,4-dichlorophenyl | " | " | (42–44) |
| 15 | 3,4-dichlorophenyl | " | " | $n_D^{27}$ 1.5988 |
| 16 | 2,4,6-trichlorophenyl | " | " | (82–84) |
| 17 | 2,4,6-trimethylphenyl | " | " | $n_D^{26}$ 1.5469 |

TABLE 1-continued

Structural Formula $R_1 \underset{N-X}{\overset{N}{\underset{\|}{=}}} (A)_n-(B)_m-(D)_l-R_2$

| Compound No. | $R_1$ | X | $-(A)_n-(B)_m-(D)_l-$ | $R_2$ | Physical Properties ( ) m.p. |
|---|---|---|---|---|---|
| 18 | 3,5-dichloro-4-C₂H₅O-phenyl | " | " | " | $n_D^{26}$ 1.5610 |
| 19 | 3,5-dichloro-2-OC₂H₅-phenyl | " | " | " | $n_D^{26}$ 1.5618 |
| 20 | 3,5-dichloro-phenyl | O | —CH₂— | 4-OCH(CH₃)₂-phenyl | $n_D^{26}$ 1.5836 |
| 21 | 3,5-dichloro-4-C₂H₅S-phenyl | " | " | " | $n_D^{26}$ 1.5923 |
| 22 | 2,4-dichloro-6-C₂H₅O-phenyl | " | " | " | $n_D^{26}$ 1.5593 |

TABLE 1-continued

Structural Formula $$R_1-\overset{N}{\underset{N-X}{\parallel}}\diagdown\overset{-(A)n-(B)m-(D)l-R_2}{\underset{-(A)n-(B)m-(D)l-}{}}$$

| Compound No. | $R_1$ | X | $R_2$ | Physical Properties ( ) m.p. |
|---|---|---|---|---|
| 23 | 2,4,6-trichloro-3-ethoxyphenyl | " | " | $n_D^{26}$ 1.5640 |
| 24 | 2,6-dichloro-3-methylphenyl | " | " | (77–80) |
| 25 | " | " | 4-methoxyphenyl (—C₆H₄—OCH₃) | $n_D^{26}$ 1.5669 |
| 26 | " | " | 3-isopropoxyphenyl (—C₆H₄—OCH(CH₃)₂) | $n_D^{26}$ 1.5611 |
| 27 | " | " | 2-methyl-6-isopropoxyphenyl | $n_D^{26}$ 1.5997 |
| 28 | " | " | 4-phenoxyphenyl | (108–111) |

(Note: compound 28 R₂ shown as 4-phenoxyphenyl with adjacent tetrahydrofuryl-H structure per image)

TABLE 1-continued

Structural Formula $$R_1 \underset{N-X}{\overset{N}{\diagdown}} -(A)_n-(B)_m-(D)_l- \\ -(A)_n-(B)_m-(D)_l-R_2$$

| Compound No. | R₁ | X | | R₂ | Physical Properties (°) m.p. |
|---|---|---|---|---|---|
| 29 | 2,6-dichlorophenyl | O | —CH₂— | cyclohexyl-O-phenyl (H) | (97–99) |
| 30 | " | " | " | 4-methylphenyl-OCH(CH₃)CH₂CH₃ | (74–75) |
| 31 | " | " | " | 4-(OCCH₃, =O)phenyl | (84–85) |
| 32 | " | " | " | 4-OH-phenyl | (127–128) |
| 33 | " | " | " | 4-methylphenyl-OCH(CH₃)COOC₂H₅ | (90–92) |
| 34 | " | " | " | 4-methylphenyl-OC(=O)NHCH | (133–135) |
| 35 | " | " | " | 3-Cl-5-CF₃-2-(4-methylphenoxy)pyridine | (124–126) |

TABLE 1-continued
Structural Formula
$R_1-C(=N)-N(X)-(A)_n-(B)_m-(D)_l-$
$-(A)_n-(B)_m-(D)_l-R_2$
| Compound No. | $R_1$ | X | $-(A)_n-(B)_m-(D)_l-$ | $R_2$ | Physical Properties ( ) m.p. |
|---|---|---|---|---|---|
| 36 | 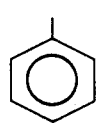 | " | " | " | $n_D^{26}$ 1.6176 |
| 37 |  | " | " | " | (75–77) |
| 38 | 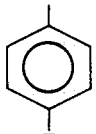 | " | " | 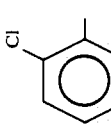 (OCOCH₃, OCOCH₃) | (117–119) |
| 39 | 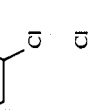 | O | $-CH_2-$ | 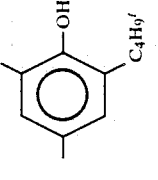 (C₄H₉ⁱ, OH, C₄H₉ⁱ) | (122–125) |
| 40 | " | " | " | 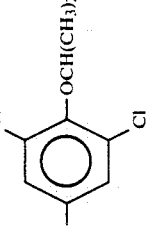 (Cl, OCH(CH₃)₂, Cl) | $n_D^{25}$ 1.5744 |
| 41 | " | " | " | 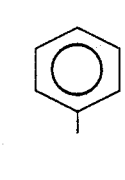 | (79–80) |

TABLE 1-continued
Structural Formula
$$R_1-\underset{N-X}{\overset{N}{\|}}\overset{(A)n-(B)m-(D)l-R_2}{\underset{(A)n-(B)m-(D)l-}{\diagdown}}$$
| Compound No. | $R_1$ | X | $R_2$ | Physical Properties ( ) m.p. |
|---|---|---|---|---|
| 42 | " | " |  —CH₃ | (82–84) |
| 43 | " | " |  —Cl | (93–95) |
| 44 | " | " | 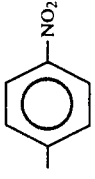 —NO₂ | (130–132) |
| 45 | " | " | 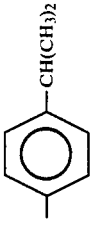 —CH(CH₃)₂ | $n_D^{26}$ 1.5727 |
| 46 | " | " | 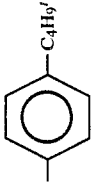 —C₄H₉ⁱ | $n_D^{26}$ 1.5622 |
| 47 | " | " | 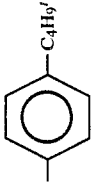 —CH₂CH(CH₃)₂ | $n_D^{26}$ 1.5641 |
| 48 | " | " | 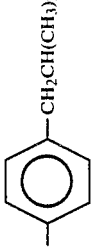 —NHCH(CH₃)₂ | (68–70) |
| 49 | " | " | 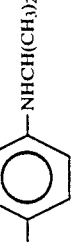 —SCH(CH₃)₂ | (47–50) |

TABLE 1-continued

Structural Formula $$R_1-\underset{N-X}{\overset{N}{\underset{\|}{\diagup}}}\overset{(A)n-(B)m-(D)l-R_2}{\underset{(A)n-(B)m-(D)l-}{\diagdown}}$$

| Compound No. | $R_1$ | X | —(A)n—(B)m—(D)l— | $R_2$ | Physical Properties ( ) m.p. |
|---|---|---|---|---|---|
| 50 | 2,6-dichlorophenyl | O | —CH₂CH₂— | 4-OCH(CH₃)₂-phenyl | $n_D^{27}$ 1.5625 |
| 51 | phenyl | " | " | " | $n_D^{25}$ 1.4365 |
| 52 | 4-methylphenyl | " | " | " | $n_D^{25}$ 1.3145 |
| 53 | 4-chlorophenyl | " | " | " | (78–80) |
| 54 | 2,4-dichlorophenyl | " | " | " | (61–62) |
| 55 | 2,6-dichlorophenyl | " | —(n = m = l = 0) | " | (90–92) |

TABLE 1-continued

Structural Formula $$R_1 \underset{N-X}{\overset{N}{\underset{\|}{\triangleleft}}} \overset{(A)n-(B)m-(D)l-R_2}{\underset{(A)n-(B)m-(D)l-}{}}$$

| Compound No. | $R_1$ | X | —(A)n—(B)m—(D)l— | $R_2$ | Physical Properties ( ) m.p. |
|---|---|---|---|---|---|
| 56 | 4-CH₃-C₆H₄ | " | " | " | (84–86) |
| 57 | 4-Cl-C₆H₄ | " | " | " | (105–107) |
| 58 | C₆H₅ | " | " | " | (55–58) |
| 59 | 2,4-Cl₂-C₆H₃ | " | " | " | (115–118) |
| 60 | 2,6-Cl₂-C₆H₃ | O | —(n = m = l = 0) | " | (122–124) |
| 61 | " | " | —CH(CH₃)— | 4-OCH₃-C₆H₄ | (84–86) |
| 62 | " | " | —CH[CH(CH₃)₂]— | 4-OCH(CH₃)₂-C₆H₄ | (103–105) |

TABLE 1-continued
Structural Formula
$R_1-\underset{N\diagdown X}{\overset{N}{\underset{\|}{\diagup}}}\overset{N}{\diagdown}\underset{-(A)n-(B)m-(D)l-}{\overset{(A)n-(B)m-(D)l-R_2}{}}$
| Compound No. | R₁ | X | —(A)n—(B)m—(D)l— | R₂ | Physical Properties ( ) m.p. |
|---|---|---|---|---|---|
| 63 | " | " | $-\underset{CH_3}{\overset{CH_3}{\underset{\|}{\overset{\|}{C}}}}-$ | " | (95-96) |
| 64 | " | " | —S—CH₂— |  p-C₄H₉ⁱ | $n_D^{25}$ 1.5893 |
| 65 | " | " | " | 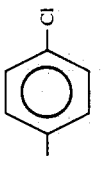 p-Cl | (95-98) |
| 66 | " | " | —NHCH₂— | " | (148-150) |
| 67 | " | " | —CH₂NH— | " | (116-118) |
| 68 | " | " | " | 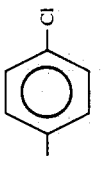 p-C₄H₉ⁱ | (104-106) |
| 69 | " | " | " | 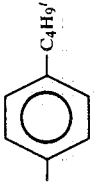 p-OCF₃ | (105-107) |
| 70 | " | " | " | 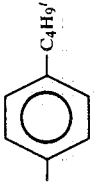 p-CH₃ | (101-103) |
| 71 | 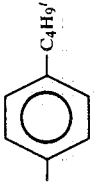 p-Cl | O | —CH₂NH— | 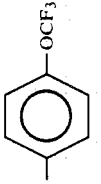 p-Cl | (100-101) |

TABLE 1-continued

Structural Formula $$R_1-\!\!\!\begin{array}{c}N\\\|\\N\end{array}\!\!\!\!-X\!\!\begin{array}{c}-(A)n-(B)m-(D)l-R_2\\-(A)n-(B)m-(D)l-\end{array}$$

| Compound No. | R₁ | X | R₂ | Physical Properties ( ) m.p. |
|---|---|---|---|---|
| 72 | " | " | 4-OCF₃-C₆H₄ | (67–69) |
| 73 | " | " | 4-CH₃-C₆H₄ | (134–136) |
| 74 | " | " | 4-C₄H₉ⁱ-C₆H₄ | (110–111) |
| 75 | 2,6-Cl₂-C₆H₃ | −C(=O)− | C₆H₅ | (98–101) |
| 76 | C₆H₅ | " | " | $n_D^{24.5}$ 1.6119 |
| 77 | 4-Cl-C₆H₄ | " | " | (107–108) |
| 78 | 4-CH₃-C₆H₄ | " | " | (101–102) |

TABLE 1-continued
Structural Formula
$$R_1 \underset{N}{\overset{N}{\rightleftarrows}} \underset{-(A)n-(B)m-(D)l-}{\overset{-(A)n-(B)m-(D)l-R_2}{\underset{X}{\bigg\langle}}}$$
| Compound No. | R₁ | X | | R₂ | Physical Properties ( ) m.p. |
|---|---|---|---|---|---|
| 79 | 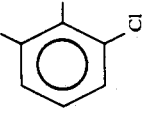 | " | —CH=CH— | " | (138–139) |
| 80 | " | " | " | 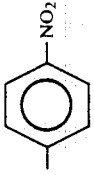 | (170–173) |
| 81 | " | " | " | 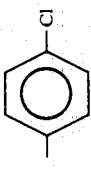 | (116–118) |
| 82 |  | O | —CH=CH— | 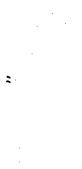 | (92–94) |
| 83 | 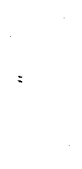 | " | " | " | (108–110) |
| 84 |  | " | " | " | (135–136) |
| 85 |  | " | " |  | (116–118) |

TABLE 1-continued
Structural Formula
$R_1\underset{N}{\overset{N}{\diagdown}}\underset{X}{\overset{}{\diagup}}{-}(A)_n{-}(B)_m{-}(D)_l{-}R_2$
| Compound No. | R₁ | X | —(A)ₙ—(B)ₘ—(D)ₗ— | R₂ | Physical Properties ( ) m.p. |
|---|---|---|---|---|---|
| 86 | " | " | " | 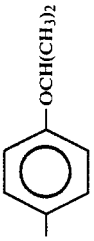—OCH(CH₃)₂ | (94–96) |
| 87 | 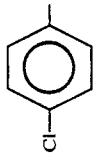 (Cl) | " | " | " | (120–122) |
| 88 | 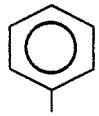 (Cl, Cl) | " | —CH— OCOCH₃ | 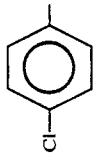 | (102–103.5) |
| 89 | " | " | —CH— OH | " | (117–117.5) |
| 90 | 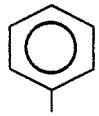 | " | " | " | (102–104) |
| 91 | 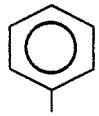 (Cl) | " | " | " | (121–124) |
| 92 | 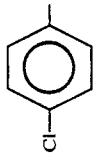 (CH₃) | " | " | " | (109–111) |

TABLE 1-continued

Structural Formula $$R_1 \underset{N}{\overset{N}{\rightleftharpoons}} \underset{X}{\overset{N}{\underset{-(A)n-(B)m-(D)l-}{\diagdown}}} \overset{(A)n-(B)m-(D)l-R_2}{\diagup}$$

| Compound No. | R₁ | X | –(A)n–(B)m–(D)l– | R₂ | Physical Properties ( ) m.p. |
|---|---|---|---|---|---|
| 93 | 2,6-diCl-phenyl (CH₃) | O | –CCH₂– (‖O) | phenyl | (206–208) |
| 94 | " | " | Cl\|–CH– | " | (66–68) |
| 95 | phenyl | " | " | " | (78–80) |
| 96 | 2,6-diCl-phenyl (CH₃) | " | OCOCH₃\|–CH– | 4-(tetrahydrofuran-2-yloxy)phenyl | (100–104) |
| 97 | " | " | OH\|–CH– | " | (112–114) |
| 98 | " | " | Cl\|–CH– | " | (116–118) |
| 99 | " | " | OCOCH₃\|–CH– | 4-OCH(CH₃)₂-phenyl | (92–96) |
| 100 | " | " | OH\|–CH– | " | (112–114) |

TABLE 1-continued

Structural Formula $$R_1 \underset{N}{\overset{N}{\Vert}} \underset{X}{\overset{N}{\diagdown}} \overset{-(A)n-(B)m-(D)l-R_2}{\underset{-(A)n-(B)m-(D)l-}{}}$$

| Compound No. | R₁ | X | —(A)n—(B)m—(D)l— | R₂ | Physical Properties ( ) m.p. |
|---|---|---|---|---|---|
| 101 | " | " | —CH(Cl)— | " | (124–126) |
| 102 | " | " | —CH(OCH₃)— | " | $n_D^{21.5}$ 1.5651 |
| 103 | " | " | —CH(OC₃H₇)— | " | $n_D^{23}$ 1.5519 |
| 104 | 2,6-dichlorophenyl | O | —CH(O-cyclohexyl)— | 4-OCH(CH₃)₂-phenyl | $n_D^{22.5}$ 1.5525 |
| 105 | " | " | —C(=O)— | " | (86–89) |
| 106 | " | " | —C(=NOH)— | " | (191–194) |
| 107 | " | " | " | " | (146–149) isomer |
| 108 | " | " | —C(=NOC₂H₅)— | " | (95–97) |
| 109 | " | " | —C(=NOCOCH₃)— | " | (110–115) |
| 110 | " | " | —C(=NOCONHCH₃)— | " | (123–125) |
| 111 | " | " | —CH₂— | cyclohexyl | (90–91) |

TABLE 1-continued

Structural Formula $$R_1 \underset{N-X}{\overset{N}{\rightleftarrows}} \begin{matrix} -(A)n-(B)m-(D)l-R_2 \\ -(A)n-(B)m-(D)l- \end{matrix}$$

| Compound No. | R₁ | X | —(A)n—(B)m—(D)l— | R₂ | Physical Properties ( ) m.p. |
|---|---|---|---|---|---|
| 112 | " | " | " | cyclopentyl-H | $n_D^{25}$ 1.5541 |
| 113 | " | " | —(n = m = l = 0) | —CH₃ | $n_D^{25}$ 1.4711 |
| 114 | 4-chlorophenyl | " | —C(=O)NH— | cyclohexyl-H | (153–155) |
| 115 | 2,6-dichlorophenyl | O | —C(=O)NH— | cyclohexyl-H | (148–149) |
| 116 | 4-chlorophenyl | " | —C(=O)—CO— | —CH₃ | (72–74) |
| 117 | 2,6-dichlorophenyl | " | " | " | (112–114) |
| 118 | | " | —CH₂— | naphthyl | (106–108) |

TABLE 1-continued
Structural Formula
$R_1 \underset{N}{\overset{N}{=}} \overset{N}{\underset{X}{\diagdown}} \overset{-(A)n-(B)m-(D)1-R_2}{\underset{-(A)n-(B)m-(D)1-}{}}$
| Compound No. | R₁ | X | –(A)n–(B)m–(D)l– | R₂ | Physical Properties ( ) m.p. |
|---|---|---|---|---|---|
| 119 | " | " | " | 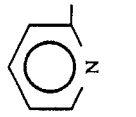 | (82–84) |
| 120 | 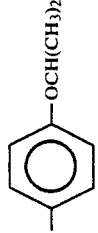 | " | " | 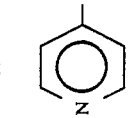—OCH(CH₃)₂ | (61–64) |
| 121 |  | " | " | " | (61–63) |
| 122 | 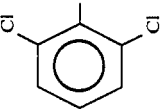 | " | " | " | (45–47) |
| 123 | CH₃— | " | " | " | $n_D^{25}$ 1.5153 |
| 124 | C₂H₅— | " | " | " | $n_D^{26}$ 1.5628 |
| 125 | CH₃–CH–CH₃ | " | " | " | $n_D^{26}$ 1.5239 |
| 126 | ⁱC₄H₉— | O | —CH₂— | 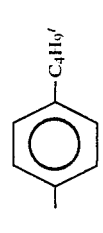—OCH(CH₃)₂ | $n_D^{27}$ 1.6574 |
| 127 | (2,6-dichlorophenyl) | S | —SCH₂— | (p-tolyl)—C₄H₉ⁱ | $n_D^{26}$ 1.6132 |

TABLE 1-continued

Structural Formula $R_1 \underset{N}{\overset{N}{\rightleftarrows}} \underset{X}{\overset{}{\rightleftarrows}} \begin{matrix} -(A)_n-(B)_m-(D)_l-R_2 \\ -(A)_n-(B)_m-(D)_l- \end{matrix}$

| Compound No. | $R_1$ | X | | $R_2$ | Physical Properties ( ) m.p. |
|---|---|---|---|---|---|
| 128 | " | " | " | 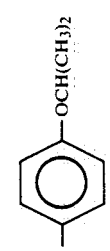 | (72–75) |
| 129 | " | O | $\underset{-CH-}{SCH_3}$ |  | (103–106) |
| 130 | " | " | $\underset{-CH-}{SC_2H_5}$ | " | (63–66) |
| 131 | " | " | $\underset{-CH-}{SCH_2COOC_2H_5}$ | " | $n_D^{30}$ 1.5692 |
| 132 | " | " | $\underset{-CH-}{OCONHCH_3}$ | " | (147–149) |
| 133 | " | " |  | " | (192–194) |
| 134 | " | " | $\underset{-CH-}{OCSNHCH_3}$ | " | $n_D^{25.5}$ 1.5993 |
| 135 | " | " | $\underset{-CH-}{OCOOC_2H_5}$ | " | (130–132) |
| 136 | " | " | $\underset{-CH-}{OCOCH_2Cl}$ | " | (85.5–87.5) |

TABLE 1-continued

Structural Formula $$R_1 \underset{N-X}{\overset{N}{\rightleftarrows}} (A)n-(B)m-(D)l-R_2$$

| Compound No. | R₁ | X | —(A)n—(B)m—(D)l— | R₂ | Physical Properties ( ) m.p. |
|---|---|---|---|---|---|
| 137 | 2,4-dichloro-6-aminophenyl (Cl, Cl, NH₂ on phenyl) | O | —CH₂— | 4-isopropoxyphenyl (—C₆H₄—OCH(CH₃)₂) | $n_D^{24}$ 1.5665 |
| 138 | 2,4-dichloro-6-(methoxymethoxy)phenyl (Cl, Cl, CH₃OCH₂O on phenyl) | " | " | " | (77–79) |
| 139 | 4-(tetrahydrofuran-2-yloxy)benzyl | " | —(n = m = l = O) | 4-chlorophenyl (—C₆H₄—Cl) | (87–89) |
| 140 | 4-chlorophenyl (—C₆H₄—Cl) | " | —CH₂— | " | (88–90) |
| 141 | 2,6-dichloro-4-(propargyloxy)phenyl (Cl, Cl, CH≡CCH₂O on phenyl) | " | " | 4-isopropoxyphenyl (—C₆H₄—OCH(CH₃)₂) | (67–68) |

TABLE 1-continued

Structural Formula $$R_1-\underset{N-X}{\overset{N}{\underset{\|}{C}}}-[(A)n-(B)m-(D)l]-R_2$$

$-(A)n-(B)m-(D)l-$

| Compound No. | $R_1$ | X | $-(A)n-(B)m-(D)l-$ | $R_2$ | Physical Properties ( ) m.p. |
|---|---|---|---|---|---|
| 142 | 2,6-dichloro-4-methylphenyl with CH(CH$_3$)$_2$ | " | " | " | $n_D^{25}$ 1.5609 |
| 143 | 2,6-dichloro-4-methylphenyl with OCH$_3$ | " | " | " | $n_D^{25}$ 1.5755 |
| 144 | 2,6-dichloro-4-methylphenyl with CH(CH$_3$)$_2$ | " | " | 4-OCH$_3$-phenyl | (68–69) |
| 145 | 2,6-dichloro-4-methylphenyl with OCH$_3$ | O | —CH$_2$— | 4-OCH$_3$-phenyl | (74–75) |
| 146 | 2,6-dichloro-4-methylphenyl | " | —CH—<br>SOCH$_3$ | 4-OCH(CH$_3$)$_2$-phenyl | (117–119) |

TABLE 1-continued
Structural Formula
$R_1 \underset{N-X}{\overset{N}{\diagup\hspace{-0.5em}\diagdown}} \underset{-(A)n-(B)m-(D)l-}{\overset{-(A)n-(B)m-(D)l-R_2}{}}$
| Compound No. | R₁ | X | –(A)n–(B)m–(D)l– | R₂ | Physical Properties ( ) m.p. |
|---|---|---|---|---|---|
| 147 | " | " | –CH– \| SO₂CH₃ | " | (125.5–127.5) |
| 148 | " | " | CH₃ \| –C– \| SCH₃ | " | (103.5–105.5) |
| 149 | " | " | –CH– \| NHCH₃ | " | (66–67.5) |
| 150 | " | " | –CH– \| N(CH₃)₂ | " | (89–92.5) |
| 151 | " | " | –CH– \| OCH₂CO₂C₂H₅ | " | $n_D^{23.5}$ 1.5425 |
| 152 | " | " | –CH– \| SCN | " | (119–120) |
| 153 | " | " | –CH– \| NH₂ | " | $n_D^{23}$ 1.5855 |
| 154 | " | " | –CH– \| F | " | $n_D^{26}$ 1.5662 |
| 155 |  | O |  |  | (119–121) |

TABLE 1-continued

Structural Formula $$R_1-\overset{N}{\underset{N-X}{\|}}\overset{(A)n-(B)m-(D)l-R_2}{\underset{-(A)m-(B)m-(D)l-}{\diagup}}$$

| Compound No. | R₁ | X | | R₂ | Physical Properties ( ) m.p. |
|---|---|---|---|---|---|
| 156 | " | " | −CH−SO₂−(C₆H₄)−CH₃ | " | (183−186.5) |
| 157 | " | " | −CH−S−(C₆H₄)−Cl | " | (114−116.3) |
| 158 | " | " | −CH−NH−(C₆H₄)−Cl | " | (173−175.5) |
| 159 | (phenyl) | " | −CH−OH | " | $n_D^{24}$ 1.5810 |
| 160 | (2,6-dichlorophenyl) | " | −CH−OCH₃ | (4-methylphenoxy, H) | $n_D^{22}$ 1.5698 |
| 161 | " | " | −CH−N(CH₃)₂ | " | $n_D^{23}$ 1.5609 |
| 162 | " | " | −CH−SCH₃ | " | (68−71.5) |

TABLE 1-continued

Structural Formula $$R_1-\underset{N-X}{\overset{N}{\underset{\|}{C}}}\underset{-(A)n-(B)m-(D)l-}{\overset{(A)n-(B)m-(D)l-R_2}{}}$$

| Compound No. | R₁ | X | —(A)n—(B)m—(D)l— | R₂ | Physical Properties ( ) m.p. |
|---|---|---|---|---|---|
| 163 | " | " | —CH—OCNHCH₃ (C=O) | " | (127–130) |
| 164 | " | " | —CH—F | " | $n_D^{21}$ 1.5708 |
| 165 | 2,6-dichlorophenyl | O | —CH—S=CNHC₂H₅ | 4-OCH(CH₃)₂-phenyl | $n_D^{23}$ 1.5812 |
| 166 | " | " | —CH—S=CNHCH₃ | " | $n_D^{23}$ 1.5851 |
| 167 | " | " | —CH—CH₃—C—CH₃—CH₂COCH₃ | " | $n_D^{21}$ 1.5471 |
| 168 | " | " | —O— | " | (86–88) |
| 169 | " | " | —S— | 4-Cl-phenyl | (147–151) |
| 170 | " | " | —CH—S=C—NH—(4-Cl-phenyl) | 4-OCH(CH₃)₂-phenyl | (146–148) |

TABLE 1-continued

Structural Formula $$R_1 \underset{N-X}{\overset{N}{\underset{\|}{=}}} \overset{N}{\underset{(A)_n-(B)_m-(D)_l-R_2}{\overset{\|}{\underset{(A)_n-(B)_m-(D)_l-}{}}}}$$

| Compound No. | R₁ | X | (A)n—(B)m—(D)l— | R₂ | Physical Properties ( ) m.p. |
|---|---|---|---|---|---|
| 171 | 4-Cl-C₆H₄ | " | —CH— S=C—NHCH₃ | " | (vis oil) |
| 172 | " | " | —CH— S=C—NH—C₆H₄-4-Cl | " | (vis oil) |
| 173 | 2,6-Cl₂-C₆H₃ | " | —S— | " | (76-80) |
| 174 | " | " | —CF₂— | " | $n_D^{27}$ 1.5438 |
| 175 | 2,6-Cl₂-C₆H₃ | O | —CH— S=CNHCH₃ | 4-Cl-C₆H₄ | (106-109) |
| 176 | 4-Cl-C₆H₄ | " | " | " | (143-145) |
| 177 | 2,6-Cl₂-C₆H₃ | " | —CH— S=C—NH—C₆H₄-4-Cl | " | (127-131) |

TABLE 1-continued

Structural Formula $$R_1 \underset{N-X}{\overset{N}{\rightleftarrows}} \begin{matrix} -(A)n-(B)m-(D)l-R_2 \\ -(A)n-(B)m-(D)l- \end{matrix}$$

| Compound No. | R₁ | X | [-(A)n-(B)m-(D)l-] | R₂ | Physical Properties ( ) m.p. |
|---|---|---|---|---|---|
| 178 | 4-Cl-C₆H₄- | " | " | " | $n_D^{22}$ 1.5471 |
| 179 | 2,6-Cl₂-C₆H₃- | " | —CF₂— | 4-OCH(CH₃)₂-C₆H₄- | (113–115) |
| 180 | 4-Cl-C₆H₄- | " | —C(=CH₂)— | " | (104–107) |
| 181 | " | " | —C(=O)— | " | (97–100) |
| 182 | " | " | —C(=NOH)— | " | (182–184) isomer |
| 183 | " | " | —C(=CH₂)— | " | (51–55) |
| 184 | 2,6-Cl₂-C₆H₃- | O | —C(=CCl₂)— | 4-OCH(CH₃)₂-C₆H₄- | $n_D^{20}$ 1.5927 |

TABLE 1-continued

Structural Formula $$R_1-\underset{N-X}{\overset{N}{\underset{\|}{\diagup}}}\overset{-(A)n-(B)m-(D)l-R_2}{\underset{-(A)n-(B)m-(D)l-}{\diagdown}}$$

| Compound No. | R₁ | X | -(A)n—(B)m—(D)l— | R₂ | Physical Properties (°) m.p. |
|---|---|---|---|---|---|
| 186 | 4-Cl-C₆H₄– | " | $-\overset{\|}{\underset{CHCH_3}{C}}=$ | " | (79–83) |
| 187 | 2,6-diCl-C₆H₃– | " | " | " | $n_D^{24}$ 1.5910 |
| 188 | " | " | " | –CCl₃ | (35–37) |
| 189 | 4-(cyclopentyloxy)benzyl | " | " | " | (91–93) |
| 190 | 2,6-diCl-C₆H₃– | " | (n = m = l = 0) | 2,6-diCl-C₆H₃– | (62–64) |
| 191 | 4-Cl-C₆H₄– | " | " | CH₃NH–C(=)–S–C₆H₃(OCH(CH₃)₂) | (184–187) |
| 192 | " | " | " | " | (170–171) |

TABLE 1-continued

Structural Formula $$R_1 \underset{N-X}{\overset{N}{\rightleftarrows}} \underset{-(A)n-(B)m-(D)l-}{\overset{(A)n-(B)m-(D)l-R_2}{}}$$

| Compound No. | R₁ | X | R₂ | Physical Properties ( ) m.p. |
|---|---|---|---|---|
| 193 | 2,6-dichlorophenyl | " | 2-[(4-chloroanilino)(2-isopropoxyphenyl)methylthio]vinyl | (195-197) |
| 194 | 4-chlorophenyl | " | 2-[(4-chloroanilino)(2-isopropoxyphenyl)methylthio]vinyl | (192-193) |
| 195 | 4-chlorobenzyl | S | 2,6-dichlorophenyl | (80-83) |
| 196 | " | " | 4-chlorophenyl | (79-81) |
| 197 | 4-isopropylbenzyl | " | 2,6-dichlorophenyl | $n_D^{21}$ 1.6022 |

TABLE 1-continued
Structural Formula
$R_1-\overset{N}{\underset{N-X}{\|}}-[(A)_n-(B)_m-(D)_l]-R_2$
| Compound No. | R$_1$ | X | $-[(A)_n-(B)_m-(D)_l]-$ | R$_2$ | Physical Properties ( ) m.p. |
|---|---|---|---|---|---|
| 198 | " | " | " | 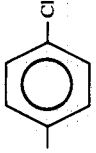 | (65–68) |
| 199 | 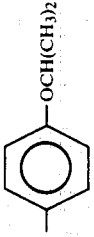 | O | —CH$_2$— | 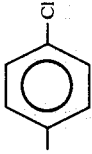 | (46–48) |
| 200 | " | " | " | 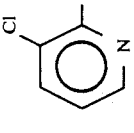 | (90–92) |
| 201 | 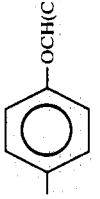 | " | " | 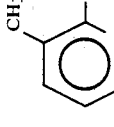 | (52–53.5) |
| 202 | " | " | " | 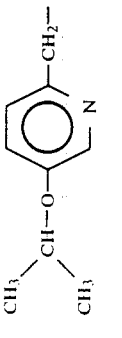 | (58–60) |
| 203 | 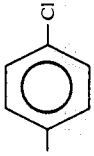 | S | —(n = m = l = 0) |  | (70–72) |

TABLE 1-continued
Structural Formula
$$R_1\underset{N\diagdown X}{\overset{N}{\underset{\|}{\bigvee}}}\overset{(A)_n-(B)_m-(D)_l-R_2}{\underset{(A)_n-(B)_m-(D)_l-}{\diagup}}$$
| Compound No. | $R_1$ | X | $-(A)_n-(B)_m-(D)_l-$ | $R_2$ | Physical Properties ( ) m.p. |
|---|---|---|---|---|---|
| 204 | 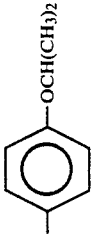 | O | $-CH_2-$ | 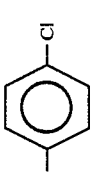 —OCH(CH$_3$)$_2$ | (41–42) |
| 205 | " | " | " |  —Cl | (95.5–97) |
| 206 | 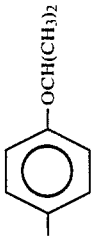 | " | " | " | (76–78) |
| 207 | " | " | " | 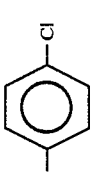 —OCH(CH$_3$)$_2$ | $n_D^{21}$ 1.5562 |
| 208 |  | " | " | " | (94–96) |
| 209 | " | " | " |  —Cl | $n_D^{22.5}$ 1.5646 |

TABLE 1-continued
Structural Formula
$R_1 - N = N$
$\phantom{R_1 - }| \phantom{=} ||$
$\phantom{R_1 - }N - X - [(A)n - (B)m - (D)l] - R_2$
$\phantom{R_1 - N - X}[(A)n - (B)m - (D)l] -$
| Compound No. | R₁ | X | R₂ | Physical Properties (°) m.p. |
|---|---|---|---|---|
| 210 | 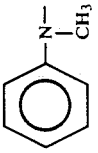 | " | " | (109–110) |
| 211 | " | " | 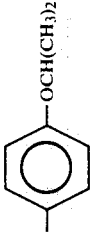 | $n_D^{31.5}$ 1.5719 |

The acaricides covered by this invention contain as active ingredients one or more types of the compounds as expressed by the general formula (1). These active ingredients, which the compounds are, may be used as-produced but normally they are used in any of the forms which ordinary agricultural chemicals can take, namely wettable powder, dust, emulsifiable concentrate, suspension concentrates or other formulations. For additives and carriers are used soybean flour, wheat flour or other vegetable flours, diatomaceous earth, apatite, gypsum, talc, pyrophyllite, clay or other fine mineral powders, when solid formulations are intended.

When liquid formulations are intended, then for solvents are used kerosene, mineral oil, petroleum, solvent naphtha, xylene, cyclohexane, cyclohexanone, dimethylformamide, dimethylsulfoxide, alcohol, acetone, water, etc. A surface active agent may, if necessary, be added in order to give a homogeneous and suitable formulation. The wettable powder, emulsifiable concentrates, flowables, etc. thus obtained are diluted with water into suspensions or emulsions of a prescribed concentration, before they are actually sprayed on plants in the field. In the case of dusts or granules, they are directly applied without further processing.

The concentration of the active ingredient in an pesticidal composition may very according to type of formulation, and is, for example, in the range of 5–70 weight percent, preferably 10–30 weight percent, in wettable powder; 5–30 weight percent, preferably 10–20 weight percent, in emulsifiable concentrate; 1–10 weight percent, preferably 2–5 weight percent in dust; 5–40 weight percent, preferably 10–30 weight percent in suspension concentrate; 1–10 weight percent, preferably 2–5 weight percent in granular formulation.

Needless to say, the compounds which this invention covers are sufficiently effective even if they are applied singly. Since these compounds are weak in adulticidal activity, however, their application in combination with one of more types of compounds having adulticidal activity against phytophagous mites, proves to be remarkably effective. In addition to adultcidally active compounds, one or more types of other agricultural chemicals may also be used in combination with the compounds of this invention.

Typical examples of acaricides or insecticides that can be used together with the compounds of this invention are as follows.

Acaricides (fungicides): BCPE chlorobenzilate, chloropropylate, proclonol, phenisobromolate, dicofol, dinobuton, binapacryl, chlorophenamidine, amitraz, BPPS, PPPS, benzomate, cyhexatin, fenbutatin-oxide, polynactin, chinomethionate, thioquinox, CPCBS, tetradifon, tetrasul, cycloprate, kayacidc, kayahope, 3-n-dodecyl-1,4-naphthoquinon-2-yl-acetate, calcium polysulfide.

Organophosphorus insecticides (acaricides): fenthion, fenitrothion, diazinon, chlorpyrifos, ESP, vamidothion, phenthoate, dimethoate, formothion, malathion, dipterex, thiometon, phosmet, menazon, dichlorvos, acephate, EPBP, dialifor, methyl parathion, oxydemethonmethyl, ethion, aldicarb, propoxur.

Pyrethroid-type insecticides (acaricides): permethrin, cypermethrin, decamethrin, fenvalerate, fenpropathrin, pyrethrin, allethrin, tetramethrine, resmethrin, pallethrin, dimethrin, proparthrin, prothrin, 3-phenoxybenzyl-2,2-dichloro-1-(4-ethoxyphenyl)-1-cyclopropanecarboxylate α-cyano-3-phenoxybenzyl-2,2-dichloro-1-(4-ethoxyphenyl)-1-cyclopropanecarboxylate
(RS)-α-cyano-3-phenoxybenzyl(RS)-2-(4-trichlormethoxypenyl)-3-methylbutylate
(RS)-α-cyano-3-phenoxybenzyl(RS)-2-(2-chloro-4-trichloromethylanilino)3-methylbutylate Machine oils Some examples of the formulations are given below. The carriers, surface-active agents, etc. that are added, however, are not limited to these examples.

EXAMPLE 13

Emulsifiable concentrate

| The compound of this invention | 10 parts |
| Alkylphenyl polyoxyethylene | 5 parts |
| Dimethyl formamide | 50 parts |
| Xylene | 35 parts |

These components are mixed and dissolved and, for use in spraying, the liquid mixture is water-diluted into an emulsion.

EXAMPLE 14

Wettable powder

| The compound of this invention | 20 parts |
| Higher alcohol sulfuric ester | 5 parts |
| Diatomaceous earth | 70 parts |
| White carbon | 5 parts |

These components are mixed and ground to fine powders, which for use in spraying, are water-diluted into a suspension.

EXAMPLE 15

Dust

| The compound of this invention | 5 parts |
| Talc | 94.6 parts |
| Silica | 0.3 part |
| Alkylphenyl polyoxyethylene | 0.1 part |

These are mixed and ground and used as-ground in spraying.

Industrial Applicability

The tests below show the acaricidal activity of the compounds of this invention.

Test 1

Control effect on desert spider mite

After being sowed in a 6 cm diameter pot, kidney beans sprouted and 7 to 10 days elapsed, their first leaves were inoculated with 30 female adults of desert spider mite resistant to organophosphorus chemicals. In the procedures of the Example 13 above, an emulsifiable concentrate of the compound of the present invention was then water-diluted to an emulsion at a concentration of 500 ppm and was sprayed on the inoculated leaves. Three days after spraying, the adults were removed. Concerning the eggs which the adults had deposited during these 3 days, an examination was conducted on the 11th day to see whether they had grown to adults. Thus the control efficacy of the acaricide was determined. The result are as shown in the following Table 2.

The control efficacy was obtained by the following formula.

Control efficacy (%) =

$$\frac{\text{No. of adults in } n\text{-}t^* \text{ area} - \text{No. of adults in } t^{**} \text{ area}}{\text{No. of adults in } n\text{-}t^* \text{ area}} \times 100$$

*n-t = non-treated
**t = treated

TABLE 2

| Compound No. | Control Efficacy (%) |
| --- | --- |
| 4 | 100 |
| 9 | 100 |
| 10 | 100 |
| 11 | 100 |
| 12 | 100 |
| 13 | 100 |
| 14 | 100 |
| 16 | 100 |
| 18 | 100 |
| 24 | 100 |
| 26 | 100 |
| 27 | 100 |
| 28 | 100 |
| 29 | 100 |
| 30 | 100 |
| 34 | 100 |
| 35 | 100 |
| 41 | 100 |
| 43 | 100 |
| 45 | 100 |
| 46 | 100 |
| 47 | 100 |
| 48 | 100 |
| 49 | 100 |
| 50 | 100 |
| 51 | 100 |
| 52 | 100 |
| 61 | 100 |
| 63 | 100 |
| 96 | 100 |
| 97 | 100 |
| 98 | 100 |
| 99 | 100 |
| 100 | 100 |
| 101 | 100 |
| 102 | 100 |
| 105 | 100 |
| 106 | 100 |
| 110 | 100 |
| 119 | 100 |
| 135 | 100 |
| 136 | 100 |
| 146 | 100 |
| 147 | 100 |
| 148 | 100 |
| 149 | 100 |
| 150 | 100 |
| 151 | 100 |
| 152 | 100 |
| 153 | 100 |
| 154 | 100 |
| 155 | 100 |
| 156 | 100 |
| 157 | 100 |
| 158 | 100 |
| 160 | 100 |
| 161 | 100 |
| 162 | 100 |
| 163 | 100 |
| 164 | 100 |
| 165 | 100 |
| 170 | 100 |
| 174 | 100 |
| 180 | 100 |
| 185 | 100 |
| 186 | 100 |
| 190 | 100 |
| 195 | 100 |

TABLE 2-continued

| Compound No. | Control Efficacy (%) |
| --- | --- |
| 197 | 100 |
| 198 | 100 |
| 199 | 100 |
| 200 | 100 |
| 201 | 100 |
| 203 | 100 |
| 204 | 100 |
| 206 | 100 |
| 207 | 100 |
| Comparative Compound* | 48 |

*Comparative Compound: 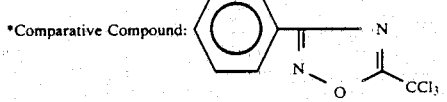

(Canadian Patent No. 713052)

We claim:

1. A compound selected from the group consisting of:
   (1) 3-(2,6-difluorophenyl)-5-(4-isopropoxybenzyl)-1,2,4-oxadiazole;
   (2) 3-(2,6-dichlorophenyl)-5-)4-isopropoxybenzyl)-1,2,4-oxadiazole;
   (3) 3-(2,6-dibromophenyl)-5-(4-isopropoxybenzyl)-1,2,4-oxadiazole;
   (4) 3-(2,6-dichlorophenyl)-5-(4-cyclopentyloxybenzyl)-1,2,4,-oxadiazole;
   (5) 3-(2,6-dichlorophenyl)-5(4-cyclohexyloxybenzyl)-1,2,4-oxadiazole;
   (6) 3-(2,6-dichlorophenyl)-5-(4-sec-butyloxybenzyl)-1,2,4-oxadiazole;
   (7) 3-(2,6-dichlorophenyl)-5(4-isopropylthiobenzyl)-1,2,4-oxadiazole;
   (8) 3-(2,6-dichlorophenyl)-5-(α-acetoxy-4-cyclopentyl oxybenzyl)-1,2,4-oxadiazole;
   (9) 3-(2,6-dichlorophenyl)-5-(α-hydroxy-4-cyclopentyl oxybenzyl)-1,2,4-oxadiazole;
   (10) 3-(2,6-dichlorophenyl)-5-(α-chloro-4-cyclopentyl oxybenzyl)-1,2,4-oxadiazole;
   (11) 3-(2,6-dichlorophenyl)-5-(α-acetoxy-4-isopropoxy benzyl)-1,2,4-oxadiazole;
   (12) 3-(2,6-dichlorophenyl)-5-(α-hydroxy-4-isopropoxy benzyl)-1,2,4-oxadiazole;
   (13) 3-(2,6-dichlorophenyl)-5-(α-dichloro-4isopropoxy benzyl)-1,2,4-oxadiazole;
   (14) 3-(2,6-dichlorophenyl)5-(4-isopropoxybenzoyl)-1,2,4-oxadiazole;
   (15) 3-(2,6-dichlorophenyl)-5-(α-hydroxyimino-4-isopropoxybenzyl)-1,2,4-oxadiazole;
   (16) 3-(2,6-dichlorophenyl-5[(N-methylcarbamoyloxy imino)-4isopropoxybenzyl]-1,2,4oxadiazole;
   (17) 3-(2,6-dichlorophenyl)5-(α-ethoxycarbonyloxy-4isopropoxybenzyl)-1,2,4-oxadiazole;
   (18) 3-(2,6-dichlorophenyl)-5-(α-dichloroacetoxy-4isopropoxybenzyl)-1,2,4-oxadiazole;
   (19) 3-(2,6-dichlorophenyl)-5(α-amino-4-isopropoxybenzyl)-1,2,4-oxadiazole; and,
   (20) 3-(4-cyclopentyloxybenzyl)-5-(2,6-dichlorophenyl)-1,2,4-oxadiazole.

2. A compound selected from the group consisting of:
   (1) 3-(2,6-dichlorophenyl)-5-(4-isopropoxybenzyl)-1,2,4-oxadiazole;
   (2) 3-(2,6-difluorophenyl)-5-(4-isopropoxybenzyl)-1,2,4-oxadiazole;
   (3) 3-(2,6-dibromophenyl-5-(4-1,2,4,-oxadiazole;

(4) 3-(2,6-dichlorophenyl)-5[(α-hydroxyimino)-4-isopropoxybenzyl]-1,2,4-oxadiazole; and,
(5) 3-(2,6-dichlorophenyl)-5-[(N-methylcarbamoyloxy imino)-4-isopropoxybenzyl]-1,2,4-oxadiazole.

3. The compound 3-(2,6-dichlorophenyl)-5-(4-isopropoxylbenzyl)-1,2,4-oxadiazole.

4. As a compound of claim 1, the compound being 3-(2,6-difluorophenyl)-5(4-isopropoxtbenzyl)-1,2,4oxadiazole.

5. As a compound of claim 1, the compound being 3-(2,6-dibromophenyl)-5-(4-isopropoxylbenzyl)-1,2,4-oxadiazole.

6. As a compound of claim 1, the compound being 3-(2,6-dichlorophenyl)-5(α-hydroxyimino)-4-isopropoxybenzyl)-1,2,4-oxadiazole.

7. 3-(2,6-dichlorophenyl-5[(N-methylcarbamoyloxy imino)-4-isopropoxybenzyl]-1,2,4-oxadiazole.

8. An acaricidal composition comprising as active ingredient the compound of claim 3.

9. An acaricidal composition comprising as active ingredient the compound of claim 4.

10. An acaricidal composition comprising as active ingredient the compound of claim 5.

11. An acaricidal composition comprising as active ingredient the compound of claim 6.

12. An acaricidal composition comprising as active ingredient the compound of claim 7.

* * * * *